United States Patent [19]

Shigematsu

[11] Patent Number: 4,892,094

[45] Date of Patent: Jan. 9, 1990

[54] PRESSURE RESPONSIVE DIAPHRAGM VALVE

[75] Inventor: Nobuo Shigematsu, Urawa, Japan

[73] Assignee: Shigematsu Works Co., Ltd., Tokyo, Japan

[21] Appl. No.: 273,350

[22] Filed: Nov. 18, 1988

[30] Foreign Application Priority Data

Mar. 24, 1988 [JP] Japan .............................. 63-38378[U]

[51] Int. Cl.$^4$ .............................................. A61M 15/00

[52] U.S. Cl. ........................... 128/201.28; 137/505.13; 137/510

[58] Field of Search ....................... 128/201.28, 205.19, 128/202.22, 205.24, 206.15, 207.12, 207.16; 137/505.13, 505.36, 505.37, 512.3, 513.3, 854, 81.2, 510

[56] References Cited

U.S. PATENT DOCUMENTS

| | | | |
|---|---|---|---|
| 3,973,588 | 8/1976 | Holst | 128/201.28 |
| 4,037,594 | 7/1977 | Riegel et al. | 128/201.28 |
| 4,229,832 | 10/1980 | Dickson | 128/201.28 |
| 4,250,876 | 2/1981 | Kranz | 128/202.22 |
| 4,275,723 | 6/1981 | Warncke et al. | 128/202.22 |
| 4,284,075 | 8/1981 | Krasberg | 128/201.28 |
| 4,442,835 | 4/1984 | Carnegie | 128/201.28 |
| 4,705,073 | 11/1987 | Beck | 128/205.19 |

FOREIGN PATENT DOCUMENTS

| | | | |
|---|---|---|---|
| 2131702 | 6/1984 | United Kingdom | 128/201.28 |

*Primary Examiner*—Eugene H. Eickholt

[57] ABSTRACT

A pressure responsive diaphragm valve, particularly suitable for a respiration responsive valve for a respirator mask. The whole of the valve assembly body is constituted by the mutually laminated layer members and assembled by simply tightening the layer members together. All of the layer members can be made by molding, without machining.

6 Claims, 9 Drawing Sheets

PRESSURE RESPONSIVE DIAPHRAGM VALVE

FIELD OF THE INVENTION

The present invention relates to a pressure responsive diaphragm valve and more particularly to a pressure responsive diaphragm valve for a respirator mask.

DESCRIPTION OF THE PRIOR ART

Because the pressure responsive diaphragm valve of the prior art has complicated constructions, it requires a considerable amount of machining process and assembling man-hours to manufacture such pressure responsive diaphragm valve and it cannot be mass-produced at a low cost. Furthermore, because such known pressure responsive diaphragm valves are made of metalic materials and therefore are relatively heavy, it is too heavy in particular to be installed on a respiratory mask and the like.

SUMMARY OF THE INVENTION

An object of the present invention is to provide a pressure responsive diaphragm valve which is light and yet can be mass-produced at a low cost and is particularly suitable to be used as a pressure responsive valve for a positive pressure type respiratory mask, that is, as a respiration responsive valve.

Another object of the present invention is to provide a pressure responsive diaphragm valve which does not require almost any of the costly machining process and can be assembled easily.

A feature of the present invention is that the valve assembly except the mounting ring (18) can be assembled by simply tightening the layer members together thereby to simplify the construction of the valve assembly.

A further feature of the present invention is to form each layer member as a completed part by molding. That is to say, the molding is employed to eliminate the machining process after molding.

Another feature of the present invention is so that the pressure detecting chamber 133 detects changes in pressure within the respirator mask through a small venting hole thereby preventing uncomfortable noise generated by the irregular vibration (attenuating vibration) of the pressure detecting diaphragm.

Further another feature of the present invention is to embed a ring element, which is harder than the diaphragm valve plate, on the side opposite to the valve throat of the annular tightened portion of the diaphragm valve plate 10, which is made of elastic material such as silicon rubber, so that the diaphragm valve plate automatically comes in contact with the valve seat by the internal stress generated in the diaphragm valve plate, that is, without the use of a spring and the like.

According to the present invention, it is possible to construct the valve assembly by molding all the layer parts which construct the main valve body and by simply tightening the layer parts together without machining. Therefore, the manufacturing cost of the valve assembly can be reduced considerably.

When the present invention is applied to the respiration responsive valve and if the air supply hose is removed from the hose mounting opening of the respiration responsive valve, the diaphragm valve plate 10 automatically comes in close contact with the valve seat by the internal stress of the diaphragm valve plate 10 so as to close the valve throat. Therefore, the present invention can eliminate the check valve which was necessary for the known respiration responsive valve.

A preferred embodiment according to the present invention will hereafter be described in connection with the respiration responsive valve for the positive pressure type respirator device shown in the accompanying drawings to which the present invention is applied.

DESCRIPTION OF THE PREFERRED EMBODIMENT

Figure 1:
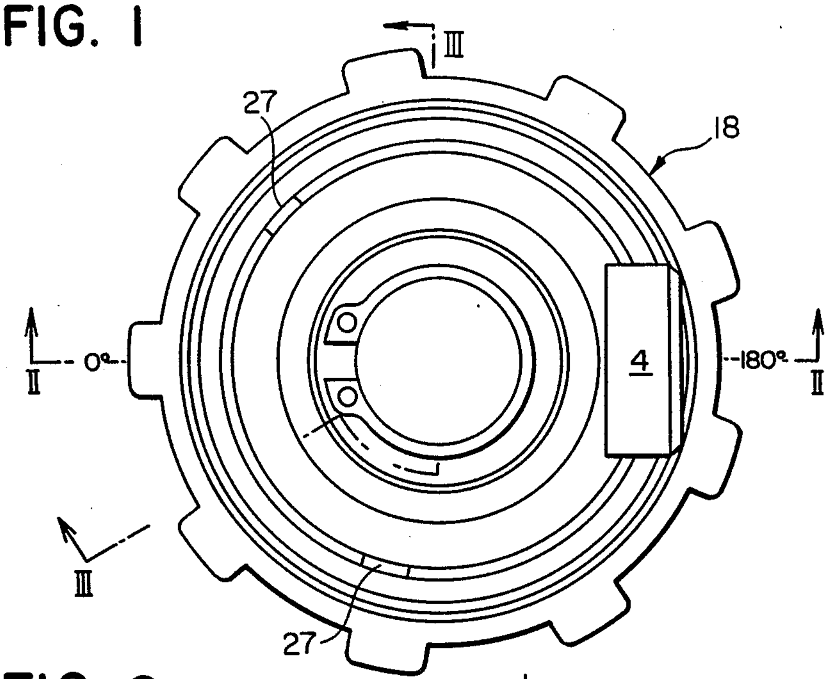
FIG. 1 is a top view of the respiration responsive valve according to the present invention.
Figure 2:
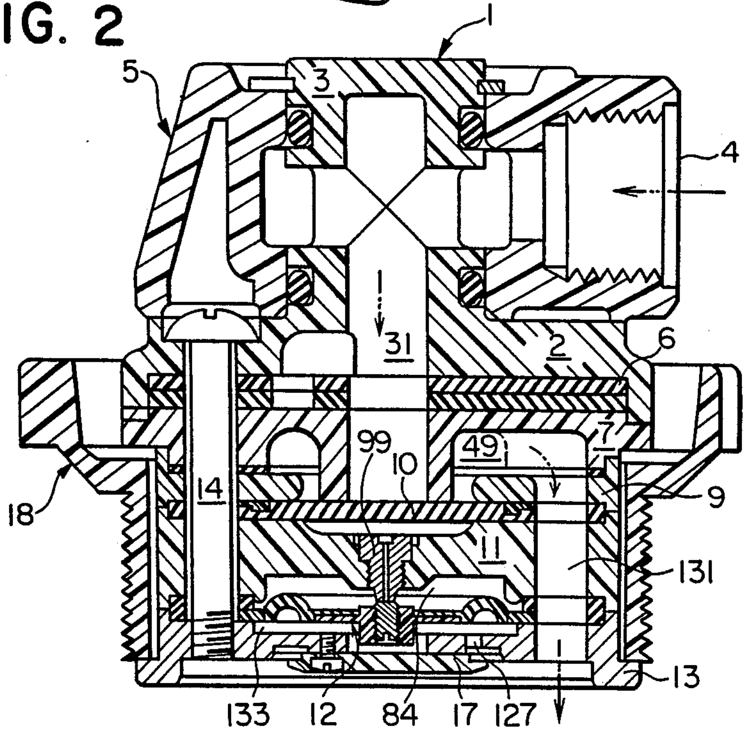
FIG. 2 is an enlarged vertical sectional view taken along the line II—II of FIG. 1.
Figure 3:
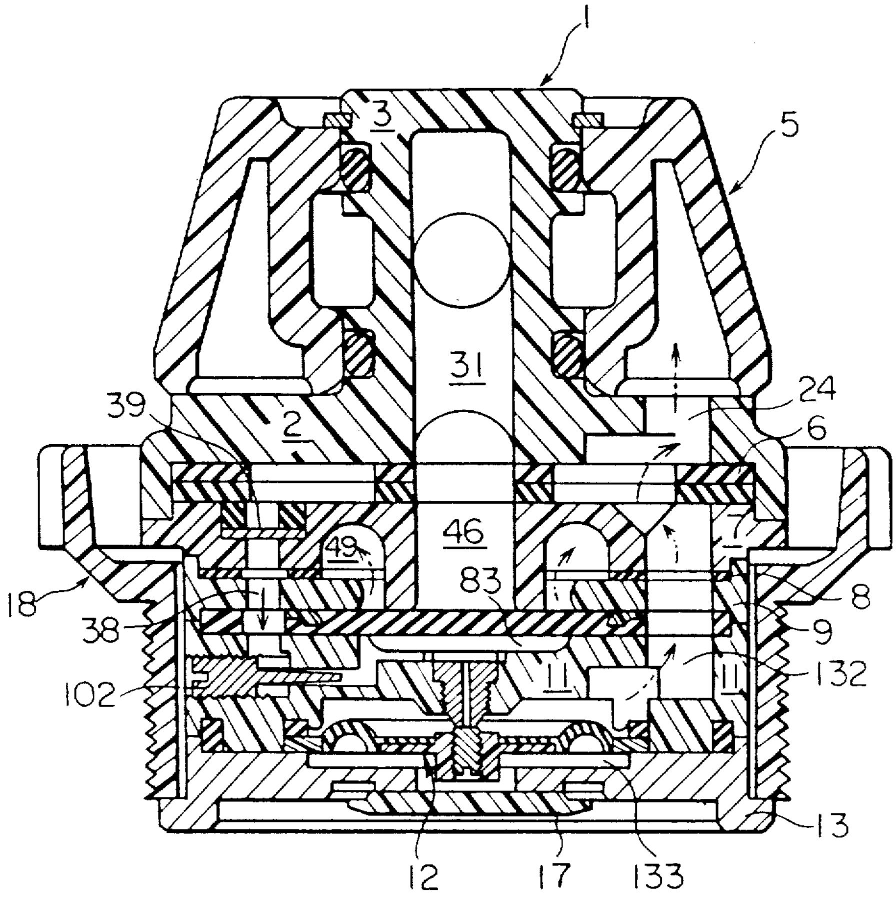
FIG. 3 is an enlarged vertical sectional view taken along the line III—III of FIG. 1.

In FIGS. 1 to 3, 1 denotes an air supply head. The air supply head 1 comprises a circular base section 2 and a cylindrical column section 3 which rises upward from the top center area of the circular base section 2, and the column section 3 is externaly fitted with the rotary joint 5 which has the air supply hose mounting opening 4. Sequentially arranged in layers under the circular base section 2 of the air supply head are the filter 6, valve box plate 7, gasket plate 8, valve chamber shaping plate 9, diaphragm valve plate 10, operating chamber plate 11, pressure detecting diaphragm 12, and protection plate 13, all of which are tightened together by three screws 14, 15, 16 which are screwed in the protection plate 13 through each of through holes formed in each of said layer members from the top of the circular base section 2 of the air supply head so as to construct the valve body. Numeral 17 is a circular cover plate mounted on the protection plate 13 in order to close the operating pressure regulating hole 115 (refer to FIG. 20 and FIG. 21) of the protection plate 13, 18 is the mounting ring with thread which is fitted externally on the main valve body so as to rotate freely. The diaphragm valve plate 10 (refer to FIG. 2 and FIG. 3) is operated so as to open and close the valve throat 46 according to the change in pressure within the operating chamber 83 into which pressurized air is supplied through a pressurized air passage 38 and a needle valve 102 which are continuously connected to the air supply passage 31 of the air supply head 1. The valve chamber 49 of the valve box plate 7 is continuously connected to the three air supply passage 131. Each of the air supply passages penetrates the protection plate 13 and is opened at inner side of the valve assembly, that is, within the mask. The pressurized air in the operating chamber 83 flows out into a exhaust chamber 84 through a pilot nozzle 99. The exhaust chamber 84 is continuously connected to the two exhaust passages 132 and is led to the open air.

Figure 4:
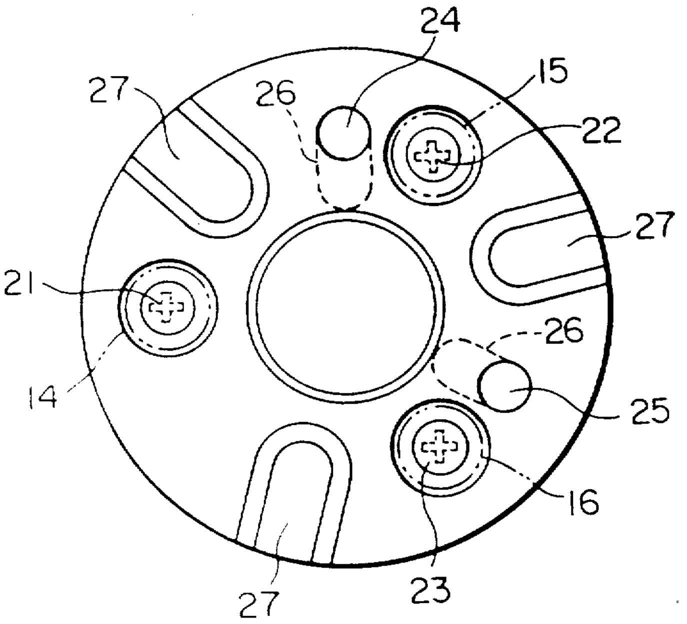
FIG. 4 is a plan view of the air supply head.

FIG. 4 is a plan view of the air supply head. The circular base section 2 of the air supply head is provided with three screw inserting holes 21, 22, 23 and two exhaust holes 24, 25, which are arranged on a circle coaxial with its axis. Each screw inserting hole and each exhaust hole are respectively extended in parallel with the axis of the circular base section 2. The lower part of each exhaust hole is continuously connected to the radial concave groove 26 formed radially on the back of the circular base section 2. Numeral 27 is the exhaust groove formed radially on the upper surface of the circular base section.

Figure 5:
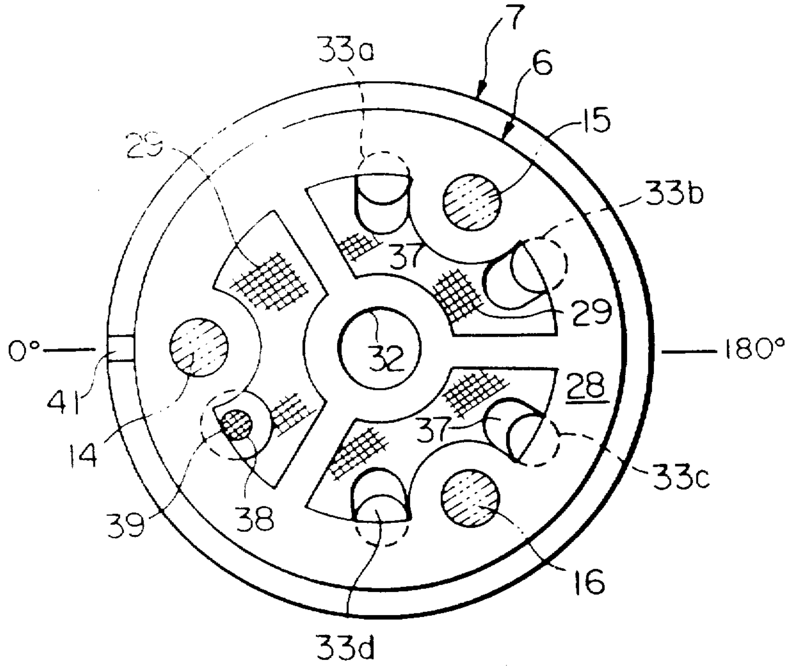
FIG. 5 is a top view of the respiration responsive valve according to the present invention from which the air supply head 1 and the mounting ring 18 are removed.

FIG. 5 is a top view of the respiration responsive valve according to the present invention, of which the air supply head 1 and the mounting nut 18 are removed. The filter 6 consists of the nonpermeable dustproof net retaining plate 28 of silicon rubber or the like and the sheet-like dustproof net 29 which closes the notched sectorial opening of the net retaining plate 28, and is laminated on the upper surface of the valve box plate 7.

At the center of the dustproof net retaining plate 28 is formed a through hole 32 which fits the air supply passage 31 of the air supply head 1. In FIG. 5, 33*a*, 33*b*, 33*c*, 33*d* are exhaust through holes formed in the valve box plate 7, 37 is the radial concave groove formed on the upper surface of the valve box plate 7 radially inward from each of said exhaust through-hole. 38 is a passage of the pressurized air for valve operation, which extend downward from the upper surface of the valve for plate 7, 39 is the filter material provided in the passage of the pressurized air for valve operation, and 41 is the positioning boss which is formed on the upper peripheral edge of the valve box plate 7 and fits into the positioning concavity formed on the lower peripheral edge of the circular base section 2 of the air supply head.

Figure 6:
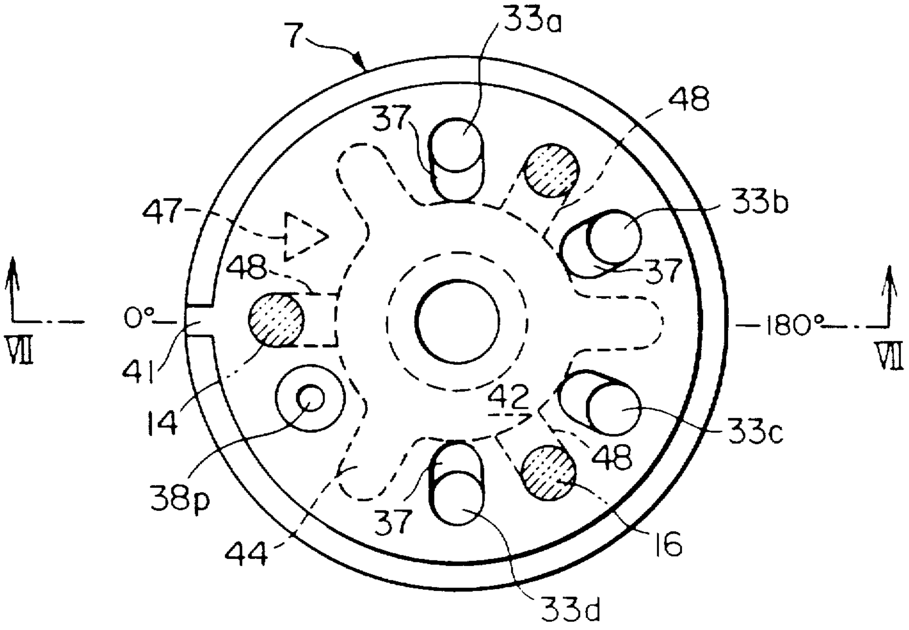
FIG. 6 is a top view similar to FIG. 5, from which the filter 6 is removed.
Figure 7:
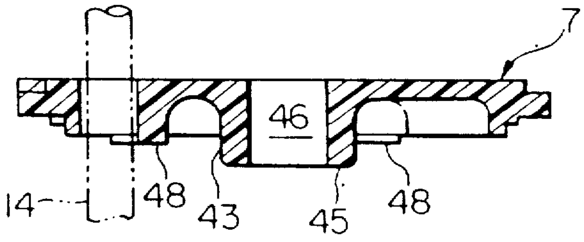
FIG. 7 is a vertical sectional view of the valve box plate 7 taken along the line VII—VII of FIG. 6.

FIG. 6 is a view similar to FIG. 5, from which the filter 6 is removed, and FIG. 7 is the cross-sectional view of the valve box plate 7 taken along the line VII—VII of the FIG. 6. On the under side of the valve box plate 7 is formed the circular concavity 42 concentrically on the axis of the valve box plate 7, and a valve cylinder section 43 protrudes downward from the bottom center of said circular concavity. The circular concavity 42 has the tongue-like concavity 44 which extends radially outward at angular positions of 60°, 180° and 240° from the positioning boss 41. At the lower end of the valve cylinder section 43 is formed the valve seat 45 which is contacted and detached by the diaphragm plate 10. In FIG. 6 and FIG. 7, 47 is a triangular positioning boss formed under the valve box plate 7 and 48 is the radial boss for controlling the tightening of the gasket which extends radially in almost the same width as the diameter of the screw inserting hole formed between the screw inserting hole and the circular concavity on under side of the valve box plate 7.

Figure 8:
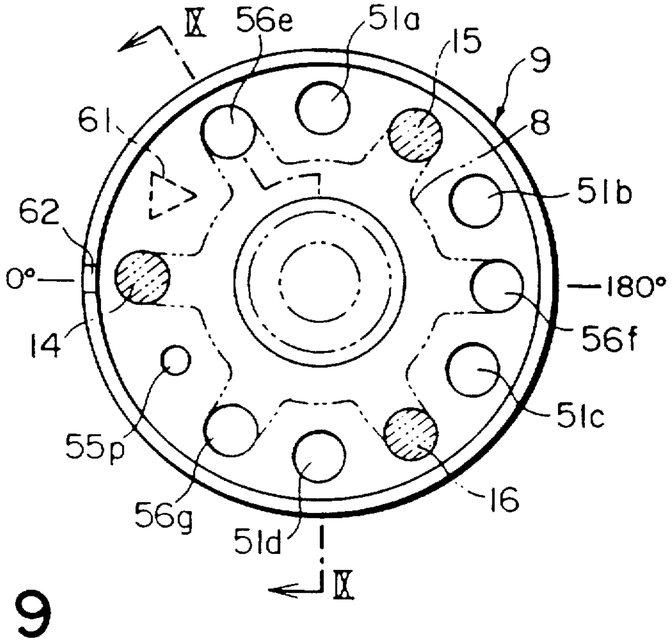
FIG. 8 is a top view similar to FIG. 6, from which the valve box plate and the gasket plate are removed, provided that the gasket plate is shown by alternate long and two short dash lines to help understanding.
Figure 9:
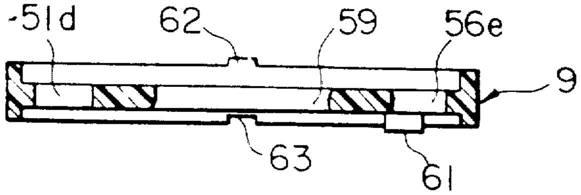
FIG. 9 is a vertical sectional view of the valve chamber shaping plate 9 taken along the line IX—IX of FIG. 8.

FIG. 8 is a view similar to FIG. 6, from which the valve box plate 7 and the gasket plate 8 are removed (note that the gasket plate is shown by alternate long and two short dash lines to help understanding), and FIG. 9 a cross-sectional view of the valve chamber shaping plate 9 taken along the line IX—IX of FIG. 8. The valve chamber shaping plate 9 is provided with inserting holes for tightening screws, exhaust through holes 51*a*, 51*b*, 51*c*, 51*d* and through holes 55*p* for pressurized air for valve operation which are, when the shaping plate 9 is laminated, continuously connected respectively to each of the exhaust through holes 33*a*, 33*b*, 33*c*, 33*d* and each of the through holes 38*p* for pressurized air for valve operation, air supply through holes 56*e*, 56*f*, 56*g* which are continuously connected respectively to the outer end of each tongue-like concavity 44 on under side of the valve box plate 7, and the circular opening 59 which defines a part of the valve chamber 49 around the valve cylinder section 43 in conjunction with the valve cylinder section 43 of the valve box plate. In FIGS. 8 to 9, 61 is the triangular positioning boss formed under the valve chamber shaping plate 9. 62 is the positioning boss formed on the upper peripheral edge of the valve chamber shaping plate 9, and 63 is the positioning concavity formed on under side of the valve chamber shaping plate 9.

Figure 10:
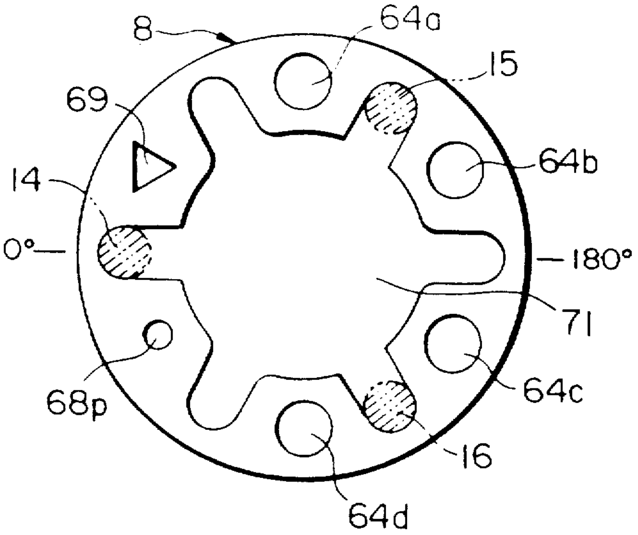
FIG. 10 is a plan view of the gasket plate 8.

FIG. 10 is the plan view of the gasket plate 8 to be arranged between the valve box plate 7 and the valve chamber shaping plate 9. The gasket plate 8 is provided with exhaust through holes 64*a*, 64*b*, 64*c*, 64*d* and a through hole 68*p* for pressurized air for valve operation which are continuously connected respectively to each of the exhaust through holes and the through hole 55*p* for pressurized air for valve operation formed in the valve box plate 7, a triangular through hole 69 into which the triangular positioning boss formed on under side of the valve box plate 7 fits, and a opening 71 which corresponds to the circular concavity, tongue-like concavity, screw inserting hole and axial boss 48 of the valve box plate 7.

Figure 11:
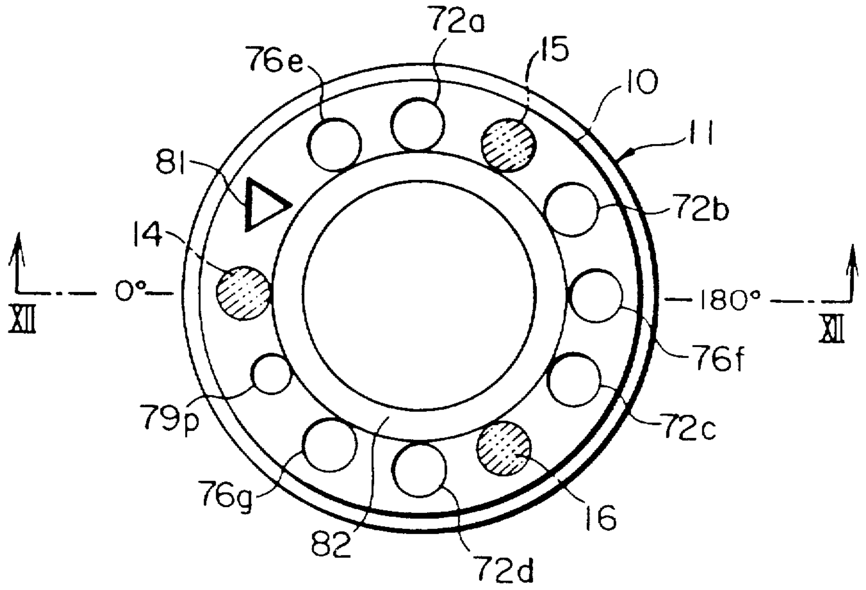
FIG. 11 is a top view similar to FIG. 8, from which the valve chamber shaping plate 9 is removed.
Figure 12:
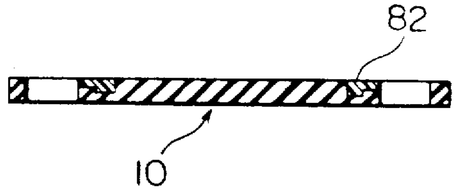
FIG. 12 is a vertical sectional view of the diaphragm valve plate taken along the line XII—XII of FIG. 11.
Figure 13:
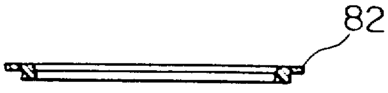
FIG. 13 is a sectional view of the ring element 82 taken along its diameter.

FIG. 11 is a view similar to FIG. 8, from which the valve chamber shaping plate 9 is removed and FIG. 12 is the cross-sectional view of the diaphragm valve plate 10 taken along the line XII—XII of FIG. 11. The diaphragm valve plate 10 is of rubber and provided with screw inserting holes, when laminated, which respectively correspond to each of the screw inserting holes of the valve chamber shaping plate 7, exhaust through holes 72*a*, 72*b*, 72*c*, 72*d*, when laminated, which are respectively connected to each of the exhaust through holes 51*a*, 51*b*, 51*c*, 51*d* of the valve chamber shaping plate 7, intake through holes 76*e*, 76*f*, 76*g*, when laminated, which are respectively connected to each of the intake holes 56e, 56f, 56g of the valve chamber shaping plate 7, and a through hole 79p for pressurized air passage, when laminated, which is connected to the through hole 55p of the valve chamber shaping plate 7, all of said holes are pubstantially arranged on a circle along circumferential edge of the diaphragm valve plate. In FIGS. 11 and 12, 81 denotes the positioning hole in which the triangular positioning boss 61 formed on under side of the valve chamber shaping plate 9 fits and 82 is a ring of synthetic resin embedded in the tightening section of the diaphragm valve plate 10. The ring element 82 works to cause the diaphragm valve plate to curve toward the valve seat 45 when the diaphragm valve plate 10 is laminated and tightened securely. FIG. 13 is a cross-sectional view of the ring 82 taken along the diameter thereof.

Figure 14:
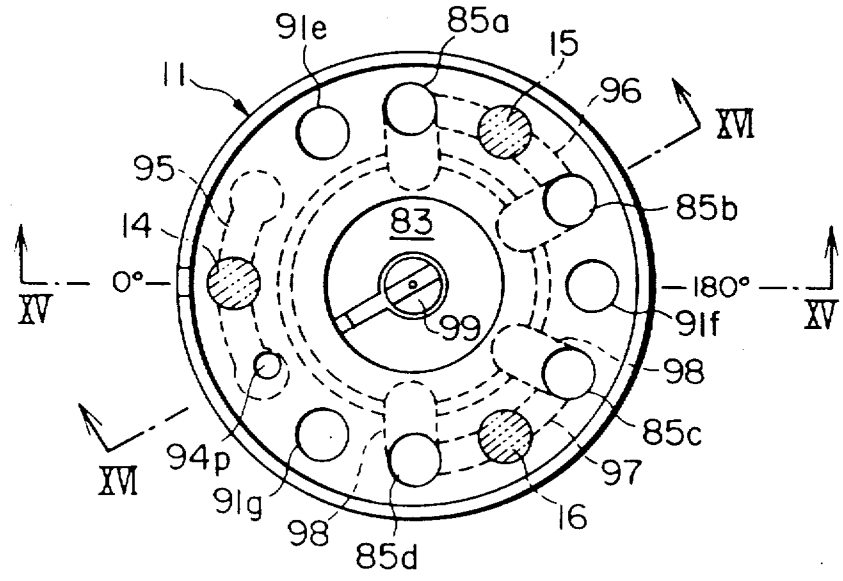
FIG. 14 is a top view similar to FIG. 11, from which the diaphragm valve plate is removed.
Figure 15:
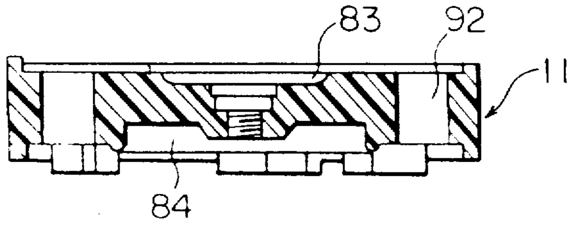
FIG. 15 is a vertical sectional view of the operating chamber plate 11 taken along the line XV—XV of FIG. 14.
Figure 16:
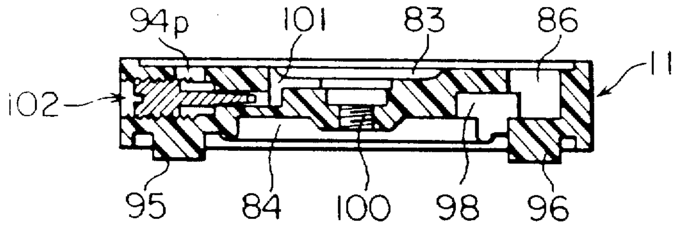
FIG. 16 is a vertical sectional view of the operating chamber plate 11 taken along the line XVI—XVI of FIG. 14.

FIG. 14 is a view similar to FIG. 11, from which the diaphragm valve plate is removed. FIG. 15 is a longitudinal sectional view of the operating chamber plate 11 taken along the line XV—XV of FIG. 14 and FIG. 16 is a longitudinal sectional view of the operating chamber plate 11 taken along the line XVI—XVI of FIG. 14. At the central part of upper side of the operating chamber plate 11 is formed a circular concavity which constitutes the operating chamber 83, and at the central part of its under side is formed a circular concavity which constitutes the exhaust chamber 84 communicated to the open air. In the outer peripheral edge portion of the operating chamber plate 11 is formed screw inserting holes, exhaust through holes 85a, 85b, 85c, 85d, intake through holes 91e, 91f, 91g, and a through hole 94p for pressurized air for valve operation, all of which respectively correspond to each of the screw inserting holes, each of the exhaust through holes, each of the intake through holes and the through hole for pressurized air of the diaphragm valve plate. Each of the exhaust through holes 85a, 85b, 85c, 85d and the through hole 94p for valve operation are not penetrated to the bottom of the operating chamber plate 11. From the bottom of the operating chamber plate 11 extrudes arc bosses 95, 96, 97 which extend from the edge of each of the screw inserting holes in both directions along the periphery of the operating chamber plate 11. In FIGS. 14 to 16, 98 denotes radial grooves formed radially on under side of the operating chamber plate which respectively connects each of the exhaust holes 85a, 85b, 85c, 85d and the exhaust chamber 84, 99 denotes a pilot nozzle which continuously connects the operating chamber 83 and the exhaust chamber 84 and which is mounted by screwing it in the mounting hole 100 at the center of the operating chamber plate, 101 denotes a pressurized airinlet, and 102 denotes a needle valve for controlling the rate of flow from the through hole 94p for pressurized air to the pressurized air inlet 101. The valve body of the needle valve 102 is screwed in the mounting hole thereof.

Figure 17:
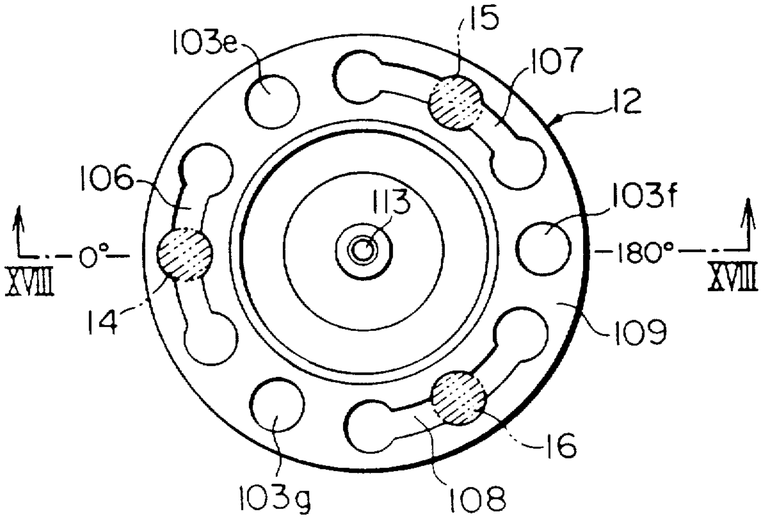
FIG. 17 is a top view of the pressure detecting diaphragm 12.
Figure 18:
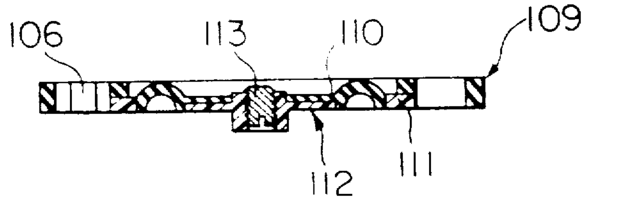
FIG. 18 is a vertical sectional view taken along the line XVIII—XVIII of FIG. 17.
Figure 19:
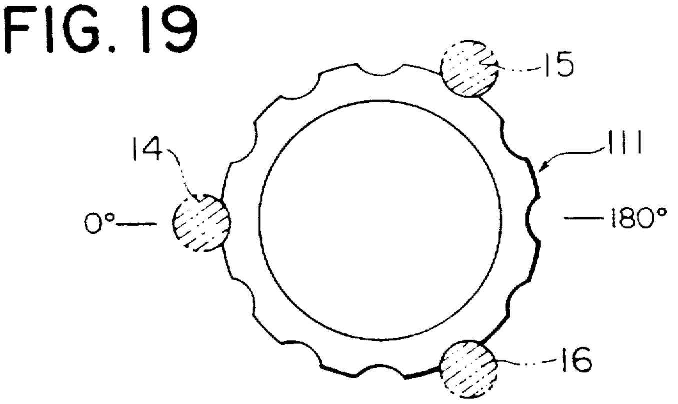
FIG. 19 is a top view of the joining ring plate 111.

FIG. 17 is a top view of the pressure detecting diaphragm 12 and FIG. 18 is a longitudinal sectional view taken along the line XVIII—XVIII of FIG. 17. The pressure detecting diaphragm 12 consists of an annular gasket section 109, a diaphragm membrane 111, a connecting ring plate which connects the annular gasket 109 and the diaphragm membrane 111, and a valve body supporting section 112 secured at the center area of the diaphragm membrane 110. The annular gasket section 109 is formed with intake through holes 103e, 103f, 103g which are respectively connected to each of the intake through holes 91e, 91f, 91g of the operating chamber plate 11; and arc openings 106, 107, 108 into which each of the arc bosses 95, 96, 97 formed under side of the operating chamber plate 11 and each of the tightening screws 14, 15, 16 are fitted. Preferably, the annular gasket section 109 and the diaphragm membrane 110 are made of rubber and the connecting ring plate 111 is made of synthetic resin. The valve body supporting section 112 consists of a cylindrical section having a threaded hole, a circular plate section extending radially from the outer periphery of the cylindrical section, and the pilot valve body 113 which is adjustably screwed in the threaded hole. The pilot valve body 113 opens and closes the outlet of the pilot nozzle 99 according to the vertical movements of the diaphragm membrane 110. FIG. 19 is a top view of the connecting ring plate 111.

Figure 20:
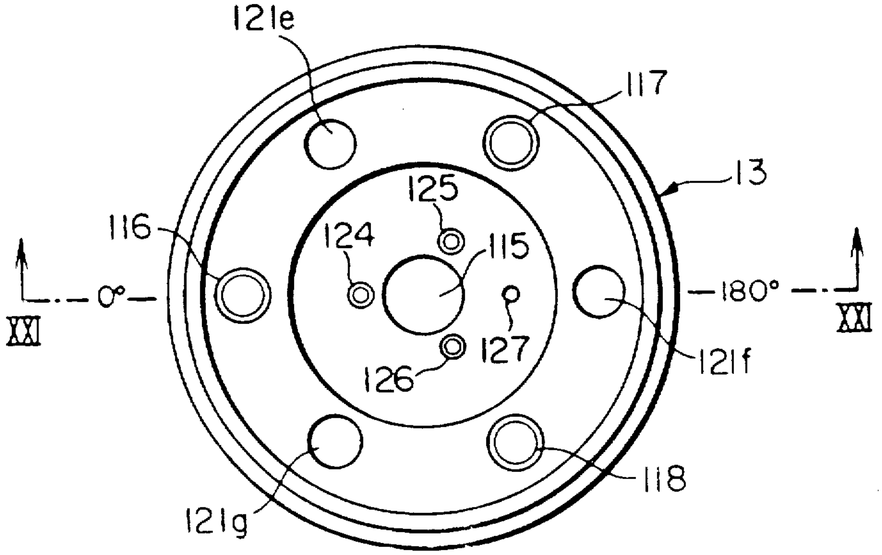
FIG. 20 is a top view similar to FIG. 14, from which the operating chamber plate 11 and the pressure detecting diaphragm 12 are removed.
Figure 21:
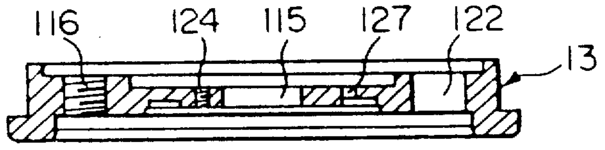
FIG. 21 is a vertical sectional view of the protection plate 13 taken along the line XXI—XXI of FIG. 20.

FIG. 20 is a view showing the upper side of the protection plate 13 similar to FIG. 14, from which the operating chamber plate 11 and the pressure detecting diaphragm 12 are removed, and FIG. 21 is a longitudinal sectional view of the protection plate 13 taken along the line XXI—XXI of FIG. 20. The protection plate 13 is formed with a center hole 115, threaded holes 116, 117, 118 which correspond to each of the screw inserting holes of the operating chamber plate 11, intake through holes 121e, 121f, 121g which correspond to each of the intake through holes of the operating chamber plate 11, threaded holes 124, 125, 126 for mounting the circular cover plate 17 arranged near the peripheral edge of the center hole 115, and small air vent 127. The cover plate 17 is mounted so as to hermetically seal the center hole 115 for adjusting the operating pressure. The protection plate 13 is preferably made of aluminum alloy but it can also be made of synthetic resin and other materials.

When the respiration responsive valve described ablve is not in use, the diaphragm valve plate 10 closes the valve throat 46 by the internal stress thereof and the pilot valve body 113 is separated from the outlet of the pilot nozzle 99.

The respiration responsive valve is hermetically mounted on the mask body of the respirator mask by screwing the threaded mounting ring 18 in the internal threads of the intake tube mounting opening of the mask body. In the hose mounting opening 4 of the respiration responsive valve is fitted an end of the respiratory air supply hose which extends from the air pump or the like.

The reason that the center hole 115 of the protection plate 13 is closed with the cover plate 17 so as to transmit the change in pressure inside the mask to the pressure detecting chamber 133 through the small air vent 127 only is to restrict irregular vibration of the pressure detecting diaphragm during valve operation thereby preventing uncomfortable noise generation and to prevent the pilot valve body 113 from being blindly operated.

The valve box plate 7 and the valve chamber shaping plate 9 may be molded integrally depending on the shape of the valve chamber.

Operations thereof will hereafter be described.

When the pressure inside the mask body is reduced during use due to the inhalation action of the user, the pressure in the pressure detecting chamber 133 which communicates with inside the mask body through the small hole 127 is reduced, the pilot valve body 113 of the pressure detecting diaphragm 12 is separated from the outlet of the pilot nozzle 99, and the pressurized air in the operating chamber 83 flows out into the exhaust chamber 84 thereby causing the pressure in the operating chamber 83 to be reduced. Such pressure reduction causes the diaphragm valve plate 10 to separate from the valve seat and the respiratory air flows through the valve throat 46, the valve chamber 49 and the three air supply passage 131 into the mask body.

When the pressure inside the mask body rises due to the exhalation action of the user subsequent to the inhalation, the pressure within the pressure detecting chamber 133 also rises and the pressure-detecting diaphragm 12 closes the pilot nozzle 99 of the operating chamber. Then, the pressure within the operating chamber, which is continuously supplied with a fixed amount of the pressurized air through the needle valve 102, rises and the diaphragm valve plate 10 closes the valve throat so that the inflow of the supplied air into the valve chamber 49, that is, the supply of the respiratory air into the mask body is stopped.

During its use, the respiration responsive valve repeats the operations described above thereby to supply the required gas for respiration to the user of the mask.

A preferred embodiment of the present invention applied to the respiration responsive valve has been described above, but the present invention can no doubt be applied to the pressure responsive diaphragm valve for other various applications. Furthermore, the present invention may be practiced by modifying differently within the scene of the claim of the present invention.

What is claimed is:

1. A pressure responsive diaphragm valve comprising a valve assembly body and a pilot nozzle that is opened or closed by action of a pressure detecting diaphragm where said detecting diaphragm is operated in accordance with a pressure variation so as to move a diaphragm valve plate to an open or closed position, and wherein said valve assembly body excluding a mounting ring of said body consists of mutually laminated layer members.

2. A pressure responsive diaphragm valve according to claim 1, characterized in that all of said laminated layer members are formed as completed members by molding, without machining.

3. A pressure responsive diaphragm valve according to claim 1, characterized in that said mutually laminated layer members are held together by a plurality of fastening means.

4. A pressure responsive diaphragm valve comprising a valve assembly body and a pilot nozzle that is opened or closed by action of a pressure detecting diaphragm where said detecting diaphragm is operated in accordance with a pressure variation so as to move a diaphragm valve plate to an open or closed position, and wherein said valve assembly body excluding a mounting ring of said body consists of mutually laminated layer members comprising an air supply head, a valve box plate, a valve chamber shaping plate, a diaphragm valve plate, an operating chamber plate, a pressure detecting diaphragm, and a protection plate.

5. A pressure responsive diaphragm valve comprising a valve assembly body and a pilot nozzle that is opened or closed by action of a pressure detecting diaphragm where said detecting diaphragm is operated in accordance with a pressure variation so as to move a diaphragm valve plate to an open or closed position, and wherein said valve assembly body excluding a mounting ring of said body consists of mutually laminated layer members, and said pressure detecting diaphragm comprises a pressure detecting chamber having a small air vent so as to detect a change in pressure thereby preventing irregular vibration of said pressure detecting diaphragm which generates uncomfortable noise.

6. A pressure responsive diaphragm valve comprising a valve assembly body and a pilot nozzle that is opened or closed by action of a pressure detecting diaphragm where said detecting diaphragm is operated in accordance with a pressure variation so as to move a diaphragm valve plate to an open or closed position, and wherein said valve assembly body excluding a mounting ring of said body consists of mutually laminated layer members and said diaphragm valve plate comprises an annular tightening section having a valve throat wherein on a side opposite said valve throat is embedded a ring element which is harder than said diaphragm valve plate, and said diaphragm valve plate automatically contacts a valve seat by internal stresses generated inside the diaphragm valve plate when the pressure detecting diaphragm is assembled into said valve assembly body.

* * * * *

UNITED STATES PATENT AND TRADEMARK OFFICE

CERTIFICATE OF CORRECTION

PATENT NO. : 4,892,094

DATED : January 9, 1990

INVENTOR(S) : Nobuo Shigematsu

It is certified that error appears in the above-identified patent and that said Letters Patent is hereby corrected as shown below:

The sheets of Drawing consisting of Figs. 3-21, should be added as per attached sheets.

Signed and Sealed this

Twenty-third Day of April, 1991

*Attest:*

HARRY F. MANBECK, JR.

*Attesting Officer*

*Commissioner of Patents and Trademarks*

273350